(12) United States Patent
Bormann et al.

(10) Patent No.: US 6,911,210 B1
(45) Date of Patent: Jun. 28, 2005

(54) STABLE ACTIVE INGREDIENT COMBINATIONS WHICH ARE EFFECTIVE AGAINST BLEMISHED SKIN AND AGAINST ACNE AND CONTAIN INTERFACE-ACTIVE GLUCOSE DERIVATIVES AND HYDROXYCARBOLIC ACIDS

(75) Inventors: Angelika Bormann, Hamburg (DE); Jens Nielsen, Henstedt-Ulzburg (DE); Andreas Herpens, Reinbek (DE); Anja Müller, Rümpel (DE); Jürgen Kielholz, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/557,376

(22) Filed: Apr. 25, 2000

(30) Foreign Application Priority Data

Apr. 29, 1999  (DE) .......................... 199 19 481

(51) Int. Cl.[7] .............. A61K 7/00; A61K 6/00; A61K 31/74; A61K 31/70; A01N 43/04
(52) U.S. Cl. ............... 424/401; 424/78.03; 424/78.08; 514/25; 514/159; 514/507; 514/557; 514/846; 514/887; 514/937
(58) Field of Search ................ 424/401, 78.03, 424/78.08; 514/25, 507, 557, 846, 887, 937, 159

(56) References Cited

U.S. PATENT DOCUMENTS

| | | | |
|---|---|---|---|
| 5,683,972 A | * 11/1997 | Zocchi | .................. 510/135 |
| 5,759,584 A | 6/1998 | Traupe et al. | |
| 5,932,234 A | 8/1999 | Simon et al. | |
| 5,961,999 A | * 10/1999 | Bimczok et al. | ............ 424/401 |
| 6,248,338 B1 | * 6/2001 | Muller et al. | ............... 424/401 |
| 2001/0028887 A1 | * 10/2001 | Douin et al. | ................ 424/401 |

FOREIGN PATENT DOCUMENTS

| | | |
|---|---|---|
| DE | 43 29 379 C1 | 2/1995 |
| DE | 0 691 126 A1 | 1/1996 |
| DE | 44 38 588 A1 | 5/1996 |
| DE | 697 00 092 T2 | 5/1999 |
| JP | 11-012157 | * 1/1999 |

* cited by examiner

*Primary Examiner*—Sreeni Padmanabhan
*Assistant Examiner*—Lauren Q Wells
(74) *Attorney, Agent, or Firm*—Norris McLaughlin & Marcus PA

(57) ABSTRACT

Use of cosmetic and/or dermatological preparations in the form of emulsions, comprising a) an effective amount of one or more α-hydroxycarboxylic acids and/or an effective amount of one or more β-hydroxycarboxylic acids
b) one or more interface-active substances, chosen from the group of glucose derivatives and, if desired, furthermore comprising (c) one or more interface-active substances chosen from the group of oligoglycerides against blemished skin or acne.

32 Claims, No Drawings

STABLE ACTIVE INGREDIENT COMBINATIONS WHICH ARE EFFECTIVE AGAINST BLEMISHED SKIN AND AGAINST ACNE AND CONTAIN INTERFACE-ACTIVE GLUCOSE DERIVATIVES AND HYDROXYCARBOLIC ACIDS

The present invention relates to active ingredients and preparations comprising such active ingredients which are effective against blemished skin and acne.

Medicinal topical compositions normally comprise one or more medicaments in an effective concentration. For the sake of simplicity, reference is made to the legal provisions of the Federal Republic of Germany (e.g. Cosmetics Directive, Foods and Drugs Act) for a clear distinction between cosmetic and medicinal use and corresponding products.

Customary forms in which cosmetics are applied are emulsions, i.e. metastable two- or multiphase systems in which the individual phases are in the liquid state. The most common emulsions are O/W and W/O emulsions. Less common application forms are multiple emulsions, i.e. those which, in the droplets of the dispersed (or discontinuous) phase, for their part comprise droplets of a further dispersed phase, e.g. W/O/W emulsions and O/W/O emulsions.

In order to be able to ensure the metastability of emulsions, interface-active substances, i.e. emulsifiers, are generally necessary.

A disadvantage of O/W emulsions in particular is often their inadequate stability towards relatively high electrolyte concentrations, which manifests itself in phase separation. Although this can sometimes lead to problems also in the case of W/O emulsions, it is by no means as significant here as in the case of O/W systems. Whilst these problems can often be overcome to a certain extent through appropriate choice of the emulsifier system, other disadvantages, however, then arise just as often.

On the other hand, it is often desirable to use certain electrolytes in order to be able to utilize their other physical, chemical or physiological properties. For example, DE-A 43 29 379 and DE-A 44 38 588 describe preparations for blemished skin or mild forms of acne which are characterized by a content of wool wax acid fractions.

In the case of blemished skin, in addition to other influences, bacterial secondary infections are of etiological importance. One of the most important microorganisms associated with blemished skin is Propionibacterium acnes.

Blemished skin and/or comedones adversely affect the wellbeing of those concerned, even in mild cases. Since virtually every teenager is affected by blemished skin to some degree, many people require this situation to be remedied.

DE 197 23 733 discloses cosmetic and dermatological emulsions having at least one aqueous phase, comprising an effective amount of one or more interface-active substances, chosen from the group of alkyl glucosides, where at least one of the aqueous phases comprises one or more electrolytes in dissolved form, where the ionic strength of the aqueous phases in which the electrolyte(s) is/are in dissolved form, is at least 0.075 mol/l.

However, this specification did not pave the way for the present invention.

An object of the present invention was therefore to reveal ways of achieving cosmetic or dermatological preparations against acne, in particular emulsions, preferably O/W emulsions which are stable towards increased electrolyte concentrations—or increased ionic strengths.

Surprisingly, it has been found, and herein lies the solution to the problem, that the use of cosmetic and/or dermatological preparations in the form of emulsions, comprising a) an effective amount of one or more α-hydroxycarboxylic acids of the general formula

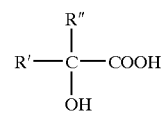

and/or an effective amount of one or more β-hydroxycarboxylic acids of the general formula

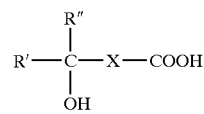

where X is an aliphatic $CH_2$ group, a cycloaliphabc CH group, an aromatic CH group or a CH(OH) group,
where in each case R' and R", independently of one another, are chosen from the group
(a1) H,
(a2) branched or unbranched $C_{1-25}$-alkyl,
(a3) branched or unbranched $C_{1-25}$-alkyl substituted by one or more carboxyl groups and/or hydroxyl groups and/or aldehyde groups and/or oxo groups (keto groups),
(a4) phenyl,
(a5) phenyl substituted by one or more carboxyl groups and/or hydroxyl groups and/or branched and/or unbranched $C_{1-25}$-alkyl groups, or where the α-carbon atom of the α-hydroxycarboxylic acid or the β-carbon atom of the β-hydroxycarboxylic acid, together with R' and X, forms an
(a6) unsubstituted cycloalkyl group having from 3 to 7 ring atoms or a
(a7) cycloalkyl group having from 3 to 7 ring atoms and substituted by one or more carboxyl groups and/or hydroxyl groups and/or oxo groups (keto groups) and/or branched and/or unbranched $C_{1-25}$-alkyl groups, and where the α-hydroxycarboxylic acid or the α-hydroxycarboxylic acids or the β-hydroxycarboxylic acid or the β-hydroxycarboxylic acids can optionally be in the form of their physiologically compatible salts and/or ethyl esters and/or methyl esters
and
b) one or more interface-active substances A, chosen from the group of glucose derivatives, which are characterized by the structural formula

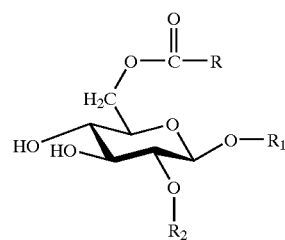

where R is a branched or unbranched alkyl radical having from 1 to 24 carbon atoms, where $R_1$ is either a hydrogen atom or a branched or unbranched alkyl radical having from 1 to 24 carbon atoms, and where $R_2$ is either a hydrogen atom or a branched or unbranched acyl radical having from 1 to 24 carbon atoms, and, if desired, furthermore comprising (c) one or more interface-active substances B, chosen from the group of substances of the general structural formula

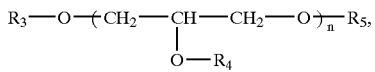

where $R_3$, $R_4$ and $R_5$, independently of one another, are chosen from the group which consists of: H, branched or unbranched, saturated or unsaturated fatty acid radicals having from 8 to 24 carbon atoms, in which up to three aliphatic hydrogen atoms can be substituted by hydroxyl groups, and n is a number from 2 to 8, against blemished skin or acne, overcomes the shortcomings of the prior art.

Emulsions obtainable according to the invention are not only surprisingly stable, they are also more effective against blemished skin and acne than would have been expected from the prior art. Moreover, they are also characterized by increased tolerability by the skin and better cosmetic appearance.

The α-hydroxycarboxylic acids used according to the invention are advantageously chosen from the following classes of substance:

(a2) α-hydroxy fatty acids, these in turn particularly advantageously being chosen from the group of $C_{10\text{-}18}$-alkylcarboxylic acids,
(a3) α-hydroxy sugar acids, aliphatic α-hydroxy fruit acids,
(a4) unsubstituted aromatic α-hydroxycarboxylic acids (e.g. mandelic acid) and
(a5) substituted aromatic α-hydroxycarboxylic acids.

The α-hydroxy fatty acids which fall under point (a2) are particularly advantageously chosen from the group consisting of α-hydroxycarboxylic acids according to the formula

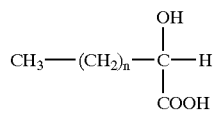

and/or
α-hydroxy-isocarboxylic acids according to the formula

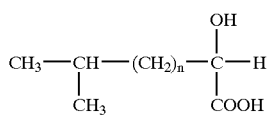

and/or
α-hydroxy-anteisocarboxylic acids according to the formula

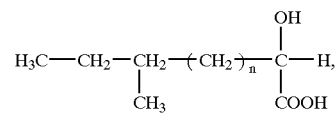

where n is in each case a number from 7 to 31.

For the purposes of the present invention, it is particularly advantageous to use α-hydroxycarboxylic acids which are $C_{16}$ substances, which carry a branched or unbranched $C_{14}H_{29}$ chain on the α-carbon atom.

It is further advantageous to use mixtures of such aliphatic α-hydroxycarboxylic acids, in particular in the form of wool wax acid mixtures in which the content of α-hydroxycarboxylic acids is 20–30% by weight, based on the overall composition.

The α-hydroxy sugar acids which fall under point (a3) are particularly advantageously chosen from the group of aldonic acids, e.g. gluconic acid, galactonic acid
aldaric acids, e.g. glucaric acid, galactaric acid (but also the fruit acid tartaric acid, which likewise falls under the definition of aldaric acid)
uronic acids, e.g. glucuronic acid, galacturonic acid
glyceric acid.

The aliphatic α-hydroxy fruit acids which fall under point (a3) are particularly advantageously chosen from the group consisting of malic acid, lactic acid, citric acid, tartaric acid.

Malic acid (hydroxysuccinic acid) is characterized by the following chemical structure:

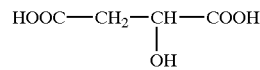

Lactic acid (2-hydroxypropanoic acid) is characterized by the following chemical structure:

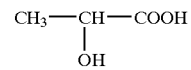

Citric acid (2-hydroxy-1,2,3propanetricarboxylic acid) is characterized by the following chemical structure:

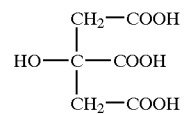

As is known, citric acid is used for buffering cosmetic and/or dermatological preparations, and also as a synergist for antioxidants in skin and hair cosmetics.

Tartaric acid (dihydroxysuccinic acid) is characterized by the following chemical structure:

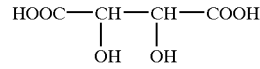

Tartaric acid, citric acid, malic acid can also be regarded as β-hydroxycarboxylic acids. A further advantageous β-hydroxycarboxylic acid is salicylic acid (also 2-hydroxybenzoic acid). It is characterized by the structure

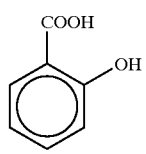

As is known, salicylic acid has an antibacterial and keratolytic action and is a constituent of some cosmetic or pharmaceutical preparations.

R of the interface-active substances A from the group of glucose derivatives is advantageously chosen from the group of unbranched alkyl radicals, preference being given to the myristyl radical, the palmityl radical, the stearyl radical and the eicosyl radical.

$R_1$ of the interface-active substances A from the group of glucose derivatives can advantageously be a hydrogen atom, but is preferably chosen from the group consisting of methyl, ethyl, propyl and isopropyl.

$R_2$ of the interface-active substances A from the group of glucose derivatives can advantageously be a hydrogen atom, but can likewise advantageously be chosen from the group consisting of myristoyl, palmitoyl, stearoyl and eicosoyl.

$R_3$ of the interface-active substances B can advantageously be a hydrogen atom, but can likewise advantageously be chosen from the group consisting of myristoyl, palmitoyl, stearoyl and eicosoyl.

$R_4$ of the interface-active substances B can advantageously be a hydrogen atom, but can likewise advantageously be chosen from the group consisting of myristoyl, palmitoyl, stearoyl and eicosoyl.

$R_5$ of the interface-active substances B can advantageously be a hydrogen atom, but can likewise advantageously be chosen from the group consisting of myristoyl, palmitoyl, stearoyl and eicosoyl.

Particularly advantageously, the interface-active substance(s) A is/are chosen from the group consisting of methylglucose monostearate (formula as below)

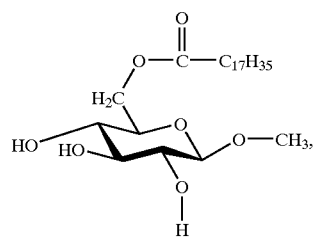

(A1)

methylglucose distearate (formula as below)

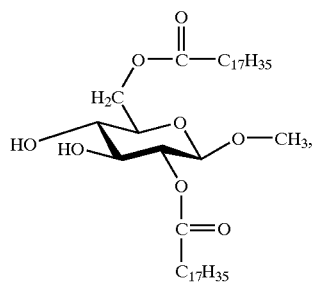

(A2)

and any mixtures thereof, for example approximately equimolar mixtures thereof, which are also referred to as methylglucose sesquistearate. Such methylglucose sesquistearate is available commercially, for example under the trade name Tego® Care PS from Th. Goldschmidt KG.

The total amount of one or more interface-active glucose derivatives used according to the invention in the finished cosmetic or dermatological preparations is advantageously chosen from the range 0.1–25.0% by weight, preferably 0.5–15.0% by weight, based on the total weight of the preparations.

It may be noted that glucosylated products are not generally pure "monoglucosides" but rather, depending on the preparation, are characterized by a degree of glucosylation DP, which is shown below on the unesterified molecule:

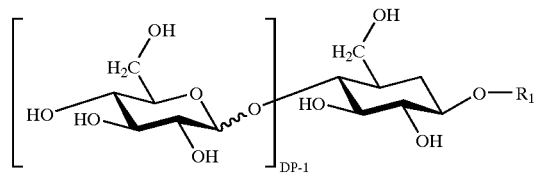

Customary degrees of glucosylation are chosen from the range 1–2, preferably 1.1–1.5, particularly preferably as approximately 1.3.

Particularly advantageously the interface-active substance(s) B is/are chosen from the group of compounds in which n assumes the value 3, and $R_3$, $R_4$ and $R_5$, independently of one another, are chosen from the group which consists of: H, branched or unbranched, saturated or unsaturated fatty acid radicals having from 14 to 20 carbon atoms, in particular the structures listed below:

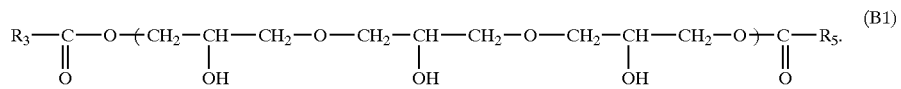

(B1)

The total amount of one or more interface-active substances B used according to the invention in the finished cosmetic or dermatological preparations is advantageously chosen from the range 0.1–25.0% by weight, preferably 0.5–15.0% by weight, based on the total weight of the preparations.

The interface-active substances A and B are advantageously present in weight ratios to one another of from 20:1 to 1:20, preferably from 10:1 to 1:10, particularly preferably from 5:1 to 1:5, very particularly preferably from 2:1 to 1:2.

According to the invention, it has proven preferable to use an approximately equimolar mixture of the compounds A2 and B1, where, in B1, the radicals $R_3$ and $R_5$ are preferably both a stearate radical. Such emulsifier combinations are, referred to collectively as "polyglyceryl(3) methylglucose distearate (PGMS), available under the trade name Tego Care® 450 from Th. Goldschmidt KG.

According to the invention, favourable, but nevertheless optional, antioxidants which can be used are all antioxidants which are customary or suitable for cosmetic and/or dermatological applications.

It is also advantageous to add antioxidants to the preparations according to the invention. The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D, L-cmosine, D-camosine, L-camosine and derivatives thereof (e.g. anserine): carotinolds, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glucosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nudeosides and salts), and sulphoximine compounds (e.g. buthionine sulphoximines, homocysteine sulphoximine, buthionine sulphones, penta-, hexa-, heptathionine sulphoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin, rutinic acid and derivatives thereof, α-glycosylrutin, ferulic acid, furfurylidene glucitol, camosine, butylhydroxytoluene, butylhydroxyanisole, nordihydroguaiac acid, nordihydroguaiaretic acid, trihydroxybutyrophenone uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nudeosides, peptides and lipids) of said active ingredients which are suitable according to the invention.

The amount of antioxidants (one or more compounds) in the preparations is preferably from 0.001 to 30% by weight, particularly preferably from 0.05 to 20% by weight, in particular 1–10% by weight, based on the total weight of the preparation.

If vitamin E and/or derivatives thereof is/are the antioxidant(s), their respective concentrations are advantageously chosen from the range 0.001–10% by weight, based on the total weight of the formulation.

It is of course known to the person skilled in the art that demanding cosmetic compositions are in most cases inconceivable without the customary auxiliaries and additives. These include, for example, bodying agents, fillers, perfume, dyes, emulsifiers, additional active ingredients, such as vitamins or proteins, sunscreen agents, stabilizers, antioxidants, insect repellents, alcohol, water, salts, and substances which have an antimicrobial, proteolytic or keratolytic action etc.

It is particularly advantageous to add buffer substances to the preparations according to the invention. In particular, it is advantageous if the preparations are buffered to a pH of 5.5 or less.

Accordingly, the compositions according to the invention can, depending on their structure, be used, for example, as barrier cream, cleansing milk, sunscreen lotion, nourishing cream, day cream or night cream etc. It is optionally possible and advantageous to use the compositions according to the invention as bases for pharmaceutical formulations.

The invention also relates to the use of the active ingredient combinations in skincare cosmetic and/or dermatological preparations.

For use, the cosmetic and dermatological preparations according to the invention are applied to the skin in a sufficient amount in a manner customary for cosmetics.

Cosmetic and dermatological preparations according to the invention can be in various forms, as are, for example, customarily used for this type of preparation. Thus, they can, for example, be a solution, an emulsion of the water-in-oil (W/O) type or of the oil-in-water (O/W) type, or a multiple emulsion, for example of the water-in-oil-in-water (W/O/W) type, a gel, a solid stick and also an aerosol.

It is also possible and advantageous for the purposes of the present invention to insert the active ingredient combinations according to the invention into aqueous systems or surfactant preparations for skin cleansing.

The cosmetic and dermatological preparations according to the invention can comprise cosmetic auxiliaries, as are customarily used in such preparations, e.g. preservatives, bactericides, perfumes, antifoams, dyes, pigments which have a colouring action, thickeners, surface-active substances, emulsifiers, softeners, moisturizers and/or humectants, fats, oils, waxes or other customary constituents of a cosmetic or dermatological formulation, such as alcohols, polyols, polymers, foam stabilizers, electrolytes, organic solvents or silicone derivatives.

If the cosmetic or dermatological preparation is a solution or lotion, solvents which can be used are:

water or aqueous solutions oils, such as triglycerides of capric or of caprylic acid, but preferably castor oil;

fats, waxes and other natural and synthetic fatty substances, preferably esters of fatty acids with alcohols of low carbon number, e.g. with isopmpanol, pmpylene glycol or glycerol, or esters of fatty alcohols with alkanoic acids of low carbon number or with fatty acids;

alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the abovementioned solvents are used. In the case of alcoholic solvents, water can be a further constituent.

Emulsions according to the invention, e.g. in the form of a barrier cream, a skin lotion, a cosmetic milk, for example in the form of a sunscreen cream or a sunscreen milk, are advantageous and comprise, for example, said fats, oils, waxes and other fatty substances, and water and an emulsifier, as is customarily used for such a type of formulation.

Preparations according to the invention can also favourably be in the form of gels which, in addition to the active ingredient combinations according to the invention and solvents customarily used therefor, customary alcohols of low carbon number, e.g. ethanol, isopropanol, 1,2-propanediol, glycerol and water or an abovementioned oil, then also comprise organic thickeners, e.g. gum arabic, xanthan gum, sodium alginate, cellulose derivatives, preferably methylcellulose, hydroxymethylcellulose, hydroxyethylcellulose, hydroxypropylcellulose, hydroxypropylmethylcellulose or inorganic thickeners, e.g. silicon dioxide and/or aluminium silicates, such as, for example, bentonites, or a mixture of polyethylene glycol and polyethylene glycol stearate or distearate. The thickener(s) is/are present in the gel, for example in an amount between 0.1 and 30% by weight, preferably between 0.5 and 15% by weight.

Solid sticks according to the invention comprise, for example, natural or synthetic waxes, fatty alcohols or fatty acid esters.

Suitable propellants for cosmetic and/or dermatological preparations according to the invention which can be sprayed from aerosol containers are the customary known readily volatile liquefied propellants, for example hydrocarbons (propane, butane, isobutane), which can be used alone or mixed with one another. Compressed air can also be used advantageously.

The person skilled in the art is of course aware that there are propellant gases which are nontoxic per se and would be suitable in principle for the present invention, but which nevertheless should be omitted because of an unacceptable impact on the environment or other accompanying circumstances, in particular fluorinated hydrocarbons and chlorofluorocarbons (CFCs).

The cosmetic or dermatological preparations according to the invention preferably comprise

| | |
|---|---|
| 0.001–0.20% | by weight of retinol and/or esters thereof |
| 0.001–5.00% | by weight of one or more α-hydroxycarboxylic acids and/or α-ketocarboxylic acids, in particular citric acid, and |
| 0.001–10.00% | by weight of one or more substances from the group of monoglycerol monocarboxylic monoesters, of diglycerol monocarboxylic monoesters, and of triglycerol monocarboxylic monoesters | in each case based on the total weight of the preparations.

They can preferably further comprise substances which absorb UV radiation in the UVB region, the total amount of filter substances being, for example, from 0.1% by weight to 30% by weight, preferably from 0.5 to 10% by weight, in particular from 1 to 6% by weight, based on the total weight of the preparations, in order to provide cosmetic and/or dermatological preparations which protect the skin from the entire region of ultraviolet radiation.

If the emulsions according to the invention comprise UVB filter substances, these can be oil-soluble or water-soluble. Examples of oil-soluble UVB filters which are advantageous according to the invention are:

3-benzylidenecamphor derivatives, e.g. 3-(4-methylbenzylidene)camphor, 3-benzylidenecamphor;

4-aminobenzoic acid derivatives e.g. 2-ethylhexyl 4-(dimethylamino)benzoate, amyl 4-(dimethylamino)benzoate;

esters of cinnamic acid, e.g. 2-ethylhexyl 4-methoxycinnamate, isopentyl 4-methoxycinnamate;

esters of salicylic acid, e.g. 2-ethylhexyl salicylate, 4-isopropylbenzyl salicylate, homomenthyl salicylate, derivatives of benzophenone, e.g. 2-hydroxy-4-methoxybenzophenone, 2-hydroxy-4-methoxy-4'-methylbenzophenone, 2,2'-dihydroxy-4-methoxybenzophenone;

esters of benzalmalonic acid, e.g. di(2-ethylhexyl) 4-methoxybenzalmalonate, 2,4,6-trianilino(p-carbo-2'-ethyl-1'-hexyloxy)1,3,5-triazine.

Examples of advantageous water-soluble UVB filters are:

salts of 2-phenylbenzimidazole-5-sulphonic acid, such as its sodium, potassium or triethanolammonium salt, and the sulphonic acid itself;

sulphonic acid derivatives of benzophenones, such as, for example, 2-hydroxy-4-methoxybenzophenone-5-sulphonic acid and its salts;

sulphonic acid derivatives of 3-benzylidenecamphor, such as, for example, 4-(2-oxo-3-bornylidenemethyl)benzenesulphonic acid. 2-methyl-5(2-oxo-3-bornylidenemethyl)sulphonic acid and its salts.

If the emulsions according to the invention comprise UVA filter substances, these can be chosen advantageously according to the invention from the group of derivatives of dibenzoylmethane, e.g. 1(4'-tert-butylphenyl)-3-(4'-methoxyphenyl)propane-1,3-dione and 1-phenyl-3-(4'-isopropylphenyl)propane-1,3-dione.

The preparations according to the invention can also comprise inorganic pigments which are customarily used in cosmetics for protecting the skin against UV rays. These are oxides of titanium, zinc, iron, zirconium, silicon, manganese, aluminium, cerium and mixtures or modifications thereof. Particular preference is given to pigments based on titanium dioxide.

Cosmetic and dermatological preparations according to the invention for use on hairy skin are, for example, shampoos, preparations which are applied during rinsing of the hair before or after shampooing, before or after permanent waving, before or after colouring or bleaching the hair, preparations for blow-drying or styling the hair, preparations for colouring or bleaching, a dressing and treatment lotion, a hairspray or a permanent wave solution.

The cosmetic and/or dermatological preparations optionally comprise additional active ingredients, auxiliaries and/or additives, as are customarily used for this type of preparation for haircare and hair treatment. Auxiliaries which can be used are preservatives, surface-active substances, antifoams, emulsifiers, thickeners, fats, oils, waxes, organic solvents, bactericides, perfumes, dyes or pigments whose task is to colour the hair or the cosmetic or dermatological preparation itself, electrolytes and additional substances for refatting the hair or the scalp.

Aqueous cosmetic cleansers according to the invention containing the active ingredient combinations according to the invention or, for aqueous cleansing, certain low-water or nonaqueous cleanser concentrates can comprise anionic, nonionic and/or amphoteric surfactants, for example conventional soaps, e.g. fatty acid salts of sodium alkyl sulphates, alkyl ether sulphates, alkane- and alkylbenzenesulphonates sulphoacetates sulphobetaines sarcosinates arridosulphobetaines sulphosuccinates sulphosuccinic monoesters alkyl ether carboxylates protein fatty acid condensates alkylbetaines and amidobetaines fatty acid alkanolamides polyglycol ether derivatives Cosmetic preparations which take the form of cosmetic skin cleansing preparations can be in liquid or solid form. They preferably comprise at least one anionic, nonionic or amphoteric surface-active substance or mixtures thereof, at least one electrolyte according to the invention and auxiliaries as are customarily used for this purpose. The surface-active substance can be present in the an cleansing preparations in a concentration between 1 and 94% by weight, based on the total weight of the preparations.

Cosmetic preparations which take the form of a shampoo comprise, in addition to an effective content of the active ingredient combinations according to the invention, preferably at least one anionic, nonionic or amphoteric surface-active substance or mixtures thereof, optionally an electrolyte according to the invention, and auxiliaries as are customarily used for this purpose. The surface-active substance can be present in the shampoo in a concentration between 1% by weight and 94% by weight If the cosmetic or dermatological preparations are in the form of a lotion which is washed out and, for example, applied before or after bleaching, before or after shampooing, between two shampooing steps, before or after permanent waving, then these are, for example, aqueous or aqueous-alcoholic solutions which optionally comprise surface-active substances, preferably nonionic or cationic surface-active substances, the concentration of which can be between 0.1 and 10% by weight, preferably between 0.2 and 5% by weight. These cosmetic and/or dermatological preparations can also take the form of aerosols with the auxiliaries customarily used for this purpose.

A cosmetic preparation in the form of a lotion which is not washed out, in particular a lotion for styling hair, a lotion which is used when blow-drying the hair, a dressing and treatment lotion, is generally in the form of an aqueous, alcoholic or aqueous-alcoholic solution and comprises at least one cationic, anionic, nonionic or amphoteric polymer or also mixtures thereof, and the active ingredient combinations according to the invention. The amount of polymers used is, for example, between 0.1 and 10% by weight, preferably between 0.1 and 3% by weight.

Cosmetic preparations according to the invention for the treatment and care of hairy skin and which comprise active ingredient combinations according to the invention can be in the form of emulsions which are of the nonionic or anionic type. In addition to water, nonionic emulsions comprise oils or fatty alcohols which may, for example, also be polyethoxylated or polypropoxylated or also mixtures of the two organic components. These emulsions optionally comprise cationic surface-active substances.

The cosmetic and dermatological preparations according to the invention can comprise cosmetic auxiliaries, as are customarily used in such preparations, e.g. preservatives, bactericides, perfumes, antifoams, dyes, pigments which have a colouring action, thickeners, surface-active substances, emulsifiers, softeners, moisturizers and/or humectants, fats, oils, waxes or other customary constituents of a cosmetic or dermatological formulation, such as alcohols, polyols, polymers, foam stabilizers, electrolytes, organic solvents or silicone derivatives.

If the cosmetic or dermatological preparation is a solution or lotion, solvents which can be used are:

water or aqueous solutions oils, such as triglycerides of capric or of caprylic acid, but preferably castor oil;

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the abovementioned solvents are used. In the case of alcoholic solvents, water can be a further constituent.

Emulsions according to the invention for nail care comprise, for example, said fats, oils, waxes and other fatty substances, and water and an emulsifier, as is customarily used for such a type of formulation.

Gels according to the invention for the care and/or repair of nails usually comprise alcohols of low carbon number, e.g. ethanol, isopropanol, 1,2-propanediol, glycerol and water or an abovementioned oil in the presence of a thickener which, in the case of oily alcoholic gels, is preferably silicon dioxide or an aluminium silicate, and in the case of aqueous-alcoholic or alcoholic gels, is preferably a polyacrylate.

In other respects, this group of cosmetic and/or dermatological preparations is subject to the customary requirements which the person skilled in the art places on such preparations and ingredients thereof.

The examples below serve to Illustrate the present invention, but are not intended to limit the content of the examples. Unless stated otherwise, the amounts are given in % by weight, based on the total weight of the respective preparations.

EXAMPLE 1

|  | % |
| --- | --- |
| Polyglyceryl-3 methylglucose distearate | 6.000 |
| Glycerol | 5.000 |
| Sorbitan stearate | 3.000 |
| Cetyl stearyl alcohol | 2.000 |
| Lactic acid | 2.000 |
| PEG-150 distearate | 0.500 |
| Xanthan gum | 0.500 |
| Sodium hydroxide | 0.450 |
| Titanium dioxide | 0.350 |
| Diazolidinylurea | 0.250 |
| Water ad | 100.00 |

EXAMPLE 2

|  | % |
|---|---|
| Titanium dioxide | 10.000 |
| Cyclomethicone | 10.000 |
| Glycerol | 10.000 |
| Polyglyceryl-3 methylglucose distearate | 4.000 |
| Sorbitan stearate | 1.000 |
| Cetyl stearyl alcohol | 6.000 |
| Lactic acid | 3.000 |
| Iron oxides | 2.000 |
| PEG-150 distearate | 2.000 |
| Xanthan gum | 0.500 |
| Sodium hydroxide | 0.450 |
| Diazolidinylurea | 0.250 |
| Bisabolol | 0.100 |
| Preservative, dyes, perfume | q.s. |
| Water ad | 100.00 |

EXAMPLE 3

|  | % |
|---|---|
| Polyglyceryl-3 methylglucose distearate | 6.000 |
| Glycerol | 5.000 |
| Sorbitan tetrastearate | 3.000 |
| Cetyl stearyl alcohol | 1.000 |
| Lactic acid | 1.000 |
| PEG-150 distearate | 0.500 |
| Xanthan gum | 0.500 |
| Sodium hydroxide | 0.450 |
| Titanium dioxide | 0.350 |
| Diazolidinylurea | 0.250 |
| Preservative, dyes, perfume | q.s. |
| Water ad | 100.00 |

EXAMPLE 4

|  | % |
|---|---|
| Polyglyceryl-3 methylglucose distearate | 5.500 |
| Glycerol | 15.000 |
| Sorbitan stearate | 3.500 |
| Cetyl stearyl alcohol | 3.000 |
| Lactic acid | 1.500 |
| PEG-150 distearate | 1.500 |
| Sodium hydroxide | 0.450 |
| Diazolidinylurea | 0.250 |
| Preservative, dyes, perfume | q.s. |
| Water ad | 100.00 |

EXAMPLE 5

|  | % |
|---|---|
| Polyglyceryl-3 methylglucose distearate | 6.000 |
| Glycerol | 5.000 |
| Sorbitan tristearate | 3.000 |
| Cetyl stearyl alcohol | 2.000 |
| Lactic acid | 2.000 |
| Xanthan gum | 0.500 |
| Sodium hydroxide | 0.450 |
| Titanium dioxide | 0.350 |
| Preservative, dyes, perfume | q.s. |
| Water ad | 100.00 |

EXAMPLE 6

|  | % |
|---|---|
| Polyglyceryl-3 methylglucose distearate | 6.000 |
| Glycerol | 5.000 |
| Sorbitan stearate | 3.000 |
| Stearyl alcohol | 2.000 |
| Lactic acid | 2.000 |
| PEG-150 distearate | 2.500 |
| Xanthan gum | 1.500 |
| Sodium hydroxide | 0.450 |
| Titanium dioxide | 0.350 |
| Diazolidinylurea | 0.250 |
| Preservative, dyes, perfume | q.s. |
| Water ad | 100.00 |

EXAMPLE 7

|  | % |
|---|---|
| Polyglyceryl-3 methylglucose distearate | 4.000 |
| Glycerol | 5.000 |
| Sorbitan distearate | 3.000 |
| Cetyl stearyl alcohol | 2.000 |
| Salicylic acid | 1.500 |
| PEG-150 distearate | 0.500 |
| Octyl methoxycinnamate | 4.000 |
| Xanthan gum | 0.500 |
| Sodium hydroxide | 0.350 |
| Titanium dioxide | 0.250 |
| Preservative, dyes, perfume | q.s. |
| Water ad | 100.00 |

EXAMPLE 8

|  | % |
|---|---|
| Polyglyceryl-3 methylglucose distearate | 6.000 |
| Glycerol | 5.000 |
| Sorbitan stearate | 3.000 |
| Behenyl alcohol | 2.000 |
| Tartaric acid | 1.000 |
| PEG-150 distearate | 1.000 |
| Xanthan gum | 0.500 |
| Sodium hydroxide | 0.450 |
| Diazolidinylurea | 0.250 |
| Preservative, dyes, perfume | q.s. |
| Water ad | 100.00 |

EXAMPLE 9

|  | % |
|---|---|
| Polyglyceryl-3 methylglucose distearate | 6.000 |
| Glycerol | 5.000 |
| Sorbitan stearate | 3.000 |
| Cetyl stearyl alcohol | 2.000 |
| Glycolic acid | 4.000 |
| PEG-150 distearate | 0.500 |
| Xanthan gum | 0.500 |
| Sodium hydroxide | 0.450 |
| Titanium dioxide | 0.350 |
| Diazolidinylurea | 0.250 |
| Preservative, dyes. perfume | q.s. |
| Water ad | 100.00 |

What is claimed is:

1. A method of treating acne comprising topically applying to acned skin an amount effective to treat said skin of a cosmetic and/or dermatological preparation in the form of an emulsion, said preparation comprising:

a) an amount effective to treat said skin of at least one hydroxycarboxylic acid selected from the group consisting of malic acid, lactic acid, citric acid, tartaric acid, salicylic acid, and glycolic acid;

b) at least one interface-active substance A selected from the group consisting of glucose derivatives of the formula:

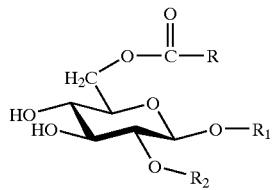

where R is a branched or unbranched alkyl radical having from 1 to 24 carbon atoms, where $R_1$ is either a hydrogen atom or a branched or unbranched alkyl radical having from 1 to 24 carbon atoms, and where $R_2$ is either a hydrogen atom or a branched or unbranched acyl radical having from 1 to 24 carbon atoms;

c) at least one interface-active substance B selected from the group consisting of substances of the formula:

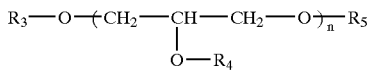

where $R_3$, $R_4$ and $R_5$ independently are selected from the group consisting of a hydrogen atom, and branched or unbranched, saturated or unsaturated fatty acid radicals having from 8 to 24 carbon atoms, in which up to three aliphatic hydrogen atoms can be substituted by hydroxyl groups, and n is a number from 2 to 8.

2. The method according to claim 1, wherein the interface-active substance A is selected from the group consisting of methylglucose monostearate (A1), methylglucose distearate (A2) and mixtures of methylglucose monostearate and methylglucose distearate.

3. The method according to claim 1, wherein the total amount of interface-active substances A in the cosmetic and/or dermatological preparation is 0.1–25.0% by weight of the preparation.

4. The method according to claim 3, wherein the total amount of interface-active substances A in the cosmetic and/or dermatological preparation is 0.5–15.0% by weight of the preparation.

5. The method according to claim 1, wherein the total amount of interface-active substances B in the cosmetic and/or dermatological preparation is 0.1–25.0% by weight of the preparation.

6. The method according to claim 5, wherein the total amount of interface-active substances B in the cosmetic and/or dermatological preparation is 0.5–15.0% by weight of the preparation.

7. The method according to claim 1, wherein the interface-active substances A and B are present in the cosmetic and/or dermatological preparation in a weight ratio of A:B of 20:1 to 1:20.

8. The method according to claim 7, wherein the interface-active substances A and B are present in the cosmetic and/or dermatological preparation in a weight ratio of A:B of 10:1 to 1:10.

9. The method according to claim 8, wherein the interface-active substances A and B are present in the cosmetic and/or dermatological preparation in a weight ratio of A:B of 5:1 to 1:5.

10. The method according to claim 9, wherein the interface-active substances A and B are present in the cosmetic and/or dermatological preparation in a weight ratio of A:B of 2:1 to 1:2.

11. The method according to claim 1, wherein the at least one hydroxycarboxylic acid is malic acid.

12. The method according to claim 1, wherein the at least one hydroxycarboxylic acid is lactic acid.

13. The method according to claim 1, wherein the at least one hydroxycaboxylic acid is citric acid.

14. The method according to claim 1, wherein the at least one hydroxycarboxylic acid is tartaric acid.

15. The method according to claim 1, wherein the at least one hydroxycarboxylic acid is salicylic acid.

16. The method according to claim 1, wherein the at least one hydroxycarboxylic acid is glycolic acid.

17. A method of treating skin blemishes due to a bacterial secondary infection comprising topically applying to skin blemishes due to a bacterial secondary infection an amount effective to treat said skin of a cosmetic and/or dermatological preparation in the form of an emulsion, said preparation comprising:

a) an amount effective to treat said skin of at least one hydroxycarboxylic acid selected from the group consisting of malic acid, lactic acid, citric acid, tartaric acid, salicylic acid, and glycolic acid;

b) at least one interface-active substance A selected from the group consisting of glucose derivatives of the formula:

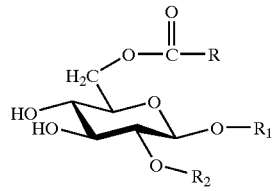

where R is a branched or unbranched alkyl radical having from 1 to 24 carbon atoms, where $R_1$ is either a hydrogen atom or a branched or unbranched allyl radical having from 1 to 24 carbon atoms, and where $R_2$ is either a hydrogen atom or a branched or unbranched acyl radical having from 1 to 24 carbon atoms;

c) at least one interface-active substance B selected from the group consisting of substances of the formula:

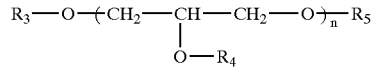

where $R_3$, $R_4$ and $R_5$ independently are selected from the group consisting of a hydrogen atom, and branched or unbranched, saturated or unsaturated fatty acid radicals having from 8 to 24 carbon atoms, in which up to thee aliphatic hydrogen atoms can be substituted by hydroxyl groups, and n is a number from 2 to 8.

18. The method according to claim 17, wherein the interface-active substance A is selected from the group consisting of methylglucose monostearate (A1), methylglucose distearate (A2) and mixtures of methylglucose monostearate and methylglucose distearate.

19. The method according to claim 17, wherein the total amount of interface-active substances A in the cosmetic and/or dermatological preparation is 0.1–25.0% by weight of the preparation.

20. The method according to claim 19, wherein the total amount of interface-active substances A in the cosmetic and/or dermatological preparation is 0.5–15.0% by weight of the preparation.

21. The method according to claim 17, wherein the total amount of interface-active substances B in the cosmetic and/or dermatological preparation is 0.1–25.0% by weight of the preparation.

22. The method according to claim 21, wherein the total amount of interface-active substances B in the cosmetic and/or dermatological preparation is 0.5–15.0% by weight of the preparation.

23. The method according to claim 17, wherein the interface-active substances A and B are present in the cosmetic and/or dermatological preparation in a weight ratio of A:B of 20:1 to 1:20.

24. The method according to claim 23, wherein the interface-active substances A and B are present in the cosmetic and/or dermatological preparation in a weight ratio of A:B of 10:1 to 1:10.

25. The method according to claim 24, wherein the interface-active substances A and B are present in the cosmetic and/or dermatological preparation in a weight ratio of A:B of 5:1 to 1:5.

26. The method according to claim 25, wherein the interface-active substances A and B are present in the cosmetic and/or dermatological preparation in a weight ratio of A:B of 2:1 to 1:2.

27. The method according to claim 17, wherein the at least one hydroxycarboxylic acid is malic acid.

28. The method according to claim 17, wherein the at least one hydroxycarboxylic acid is lactic acid.

29. The method according to claim 17, wherein the at least one hydroxycarboxylic acid is citric acid.

30. The method according to claim 17, wherein the at least one hydroxycarboxylic acid is tartaric acid.

31. The method according to claim 17, wherein the at least one hydroxycarboxylic acid is salicylic acid.

32. The method according to claim 17, wherein the at least one hydroxycarboxylic acid is glycolic acid.

* * * * *